(12) United States Patent
Porat et al.

(10) Patent No.: US 8,361,083 B2
(45) Date of Patent: Jan. 29, 2013

(54) OBSTETRICAL VACUUM EXTRACTOR WITH OVER-TRACTION RELEASE

(75) Inventors: Gadi Porat, Jerusalem (IL); Michael G. Ross, Los Angeles, CA (US); Yoram Cohen, Shoham (IL)

(73) Assignee: Michael G. Ross, Los Angeles, CA (US)

(*) Notice: Subject to any disclaimer, the term of this patent is extended or adjusted under 35 U.S.C. 154(b) by 141 days.

(21) Appl. No.: 12/849,291

(22) Filed: Aug. 3, 2010

(65) Prior Publication Data

US 2010/0318096 A1 Dec. 16, 2010

Related U.S. Application Data

(63) Continuation-in-part of application No. 12/371,263, filed on Feb. 13, 2009, now abandoned.

(60) Provisional application No. 61/028,243, filed on Feb. 13, 2008.

(51) Int. Cl.
*A61B 17/42* (2006.01)
*A61B 17/46* (2006.01)
*A61D 1/10* (2006.01)

(52) U.S. Cl. ........................................... 606/123

(58) Field of Classification Search .................. 623/119, 623/121–124, 127, 213–217; 604/73, 74–77, 604/275, 278, 279, 541, 542; 606/119, 121–124, 606/127, 213–217
See application file for complete search history.

(56) References Cited

U.S. PATENT DOCUMENTS

| | | | |
|---|---|---|---|
| 3,202,152 A | 8/1965 | Wood | |
| 3,794,044 A * | 2/1974 | Vennard et al. | 606/123 |
| 5,019,086 A | 5/1991 | Neward | |
| 5,395,379 A * | 3/1995 | Deutchman et al. | 606/123 |
| 5,693,058 A * | 12/1997 | Cavanagh et al. | 606/123 |
| 6,059,795 A | 5/2000 | Wallace | |
| 6,074,399 A | 6/2000 | Wallace | |
| 6,179,845 B1 | 1/2001 | Peters | |
| 6,355,047 B1 | 3/2002 | Wallace | |
| 6,361,542 B1 | 3/2002 | Dimitriu | |
| 6,383,163 B1 * | 5/2002 | Kelly et al. | 604/74 |
| 6,468,284 B1 | 10/2002 | Wallace | |

(Continued)

FOREIGN PATENT DOCUMENTS

WO 2004110254 12/2004
WO 2009060431 5/2009

OTHER PUBLICATIONS

Search Report for European Application No. EP11176414 dated Aug. 26, 2011.

*Primary Examiner* — Ryan Severson
*Assistant Examiner* — Katherine M Shi
(74) *Attorney, Agent, or Firm* — Fleit Gibbons Gutman Bongini & Bianco PL; Paul D. Bianco; Martin Fleit

(57) ABSTRACT

A vacuum extractor for obstetrical use comprises a vacuum cup at one end of an elongated stem having a handle at the opposite end. The vacuum cup is sealed over a portion of the head of the fetus and a vacuum source, usually operating through the stem, connects to the inner side of the cup and secures it to the fetal head. A strain sensor is connected to the stem. When the force applied to the cup through the handle and stem exceeds a predetermined maximum, a valve connecting the vacuum pressure to the atmosphere is opened so as to release the vacuum pressure from the cup. Another extractor comprises an elongated hollow stem having one or more apertures along its length, a vacuum source connected to a cup supported on the stem, and a handle member which includes a traction limiting element operative to open and close the apertures.

15 Claims, 6 Drawing Sheets

U.S. PATENT DOCUMENTS

| | | | |
|---|---|---|---|
| 6,620,171 B2 * | 9/2003 | Vines | 606/123 |
| 7,291,156 B1 | 11/2007 | Perone | |
| D639,941 S | 6/2011 | Porat et al. | |
| 2002/0032404 A1 * | 3/2002 | Silver | 604/74 |
| 2002/0165556 A1 * | 11/2002 | Wallace | 606/123 |
| 2009/0204124 A1 | 8/2009 | Ross | |

* cited by examiner

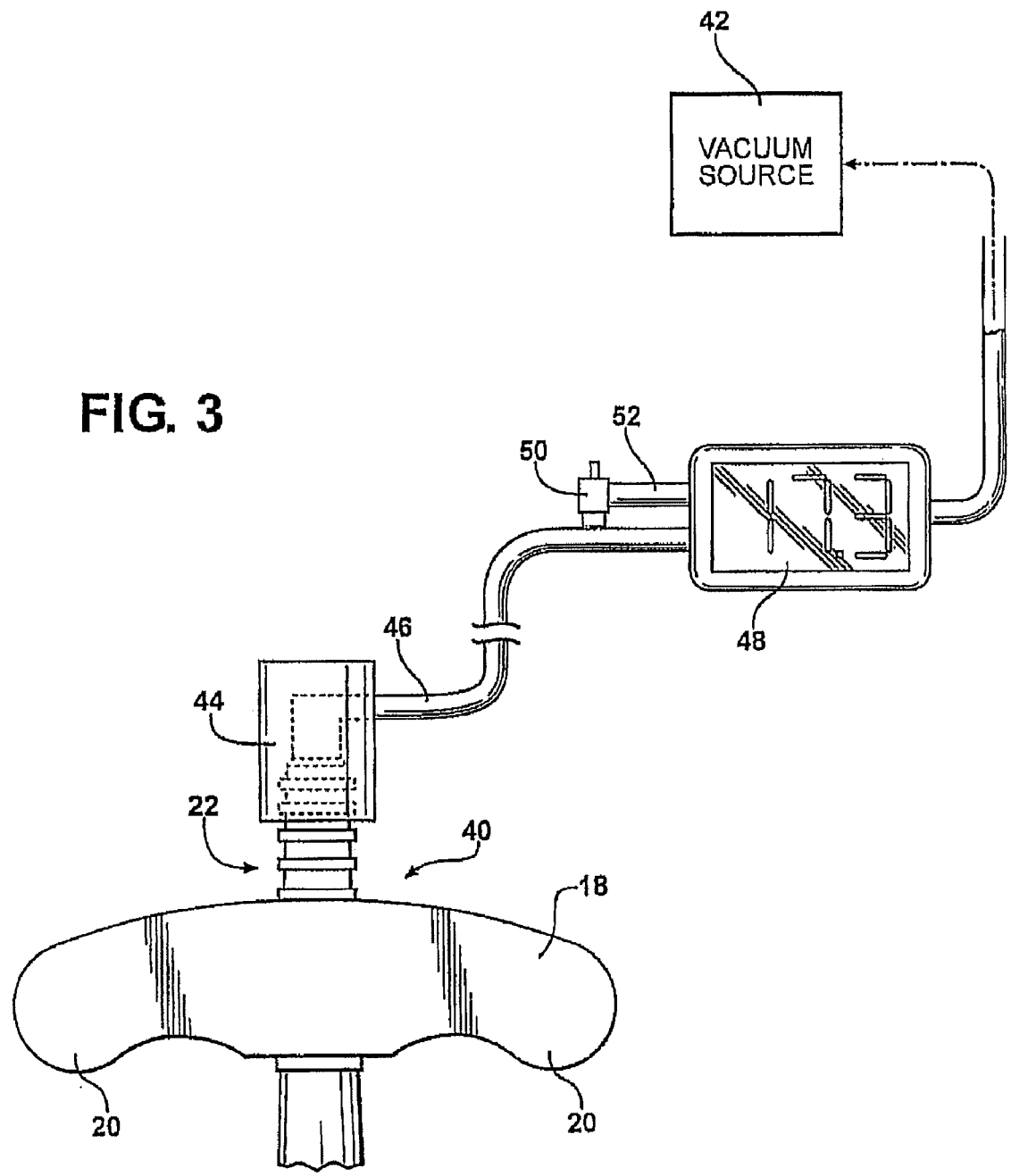

OBSTETRICAL VACUUM EXTRACTOR WITH OVER-TRACTION RELEASE

CROSS-REFERENCE TO RELATED APPLICATIONS

This application is a continuation in part of, and claims priority from, U.S. patent application Ser. No. 12/371,263, filed Feb. 13, 2009, now abandoned which in turn claims priority from U.S. Provisional Patent Application Ser. No. 61/028,243, filed Feb. 13, 2008, both of which are incorporated herein by reference.

FIELD OF THE INVENTION

This invention relates to an improved vacuum extractor for childbirth including a vacuum cup connected to a handle through a stem and more particularly to such an extractor including a traction gauge which measures the extraction force applied to the fetus through the cup and releases the vacuum on the cup when the extraction force exceeds a predetermined value.

BACKGROUND OF THE INVENTION

Vacuum extractors have long been used as a tool to assist delivery, primarily in vaginal deliveries. These extractors are often used when spontaneous vaginal delivery is not possible or is unsuccessful. They typically employ a bell shaped vacuum cup connected to a handle that is used to apply a tractive force to the cup with a tube being connected by an elongated stem. A manually or electrically powered suction device is attached to the cup either through a peripherally located vacuum port or through the stem.

In use, the surgeon attaches the open end of the vacuum cup over the fetal head. A vacuum is then drawn in the cup either through use of a manually operated vacuum pump or an electrical vacuum pump. The physician then pulls on the handle to apply a delivering force to the fetal head. The force applied to the extractor must be limited to prevent harm to the fetus. With conventional vacuum extractors reliance is placed on the physician's estimate of the force being applied to avoid the imposition of excessive forces.

It has been proposed to provide vacuum extractors incorporating sensors which measure the force applied between the vacuum cup and the handle to provide the physician with an indication of when excessive forces are being applied.

U.S. Pat. No. 6,355,047 discloses an extractor incorporating such a sensor and provides a slipping mechanism which causes the length of the force center to increase when an applied traction force exceeds a predetermined level. The physician may then use his judgment as to whether to continue to apply a greater force or to terminate use of the vacuum extractor. However, in some situations excessive force has been applied despite the incorporation of a force sensor and/or a slipping mechanism, resulting in the breaking of blood vessels connecting the fetal scalp from its underlying surface.

SUMMARY OF THE INVENTION

The present invention is accordingly directed toward an obstetrical vacuum extractor including a traction sensor connected to the air valve which releases the vacuum within the suction cup when an excessive, predetermined, force is applied to the handle of the extractor. The birthing attendant then may reattach the cup to the fetal scalp and reapply the vacuum, or resort to other means to complete the delivery. In a preferred embodiment of the invention, which will subsequently be disclosed in detail, the sensor includes a gauge operative to provide a visual indication to the user of the extraction force being exerted. The vacuum gauge may be incorporated in the conduit between the vacuum cup and the vacuum source, or alternatively it may be built into the stem, using a strain gauge or the like.

In another aspect of the invention there is provided a vacuum extractor for use by a physician in an obstetrical delivery where the extractor is in suction communication with a vacuum source. The extractor includes: an elongated hollow stem having one or more apertures along its length; an open-ended cup supported on one end of the stem with the open end directed away from the stem, the vacuum source connected to the interior of the cup so that when the one or more apertures are closed and the open end of the cup is brought into contact with the fetal scalp a vacuum secures the cup to the scalp; and a handle member disposed on the stein. The handle member includes: handle ears; and a traction limiting element in arrangement with the handle ears. The limiter is operative to open and close the one or more apertures. When no traction is applied by the physician to the handle ears the traction limiting element blocks air flow from the ambient atmosphere through the one or more apertures to the stem and when the physician applies traction to the handle ears so that the magnitude of the traction exceeds a predetermined value the traction limiting element is operative to open the one or more apertures allowing a flow of air from the ambient releasing the vacuum securing the cup to the fetal scalp.

In one embodiment of this second aspect of the invention, the handle ears of the vacuum extractor have a channel and a passage formed therein. The passage is in air flow communication via the channel with the one or more apertures of the elongated hollow stem. The traction limiting element includes: one or more pressure valves positioned in the passage disposed within one or more of the handle ears. The one or more pressure valves have a distal portion and a proximal portion, each portion having an internal diameter with the internal diameter of the distal portion being smaller than that of the proximal portion. The limiter also includes an elastic element circumscribing the one or more pressure valves, and when no traction is applied to the handle ears the proximal portion of each of the one or more pressure valves closes off the channel and the one or more apertures from the ambient. When the physician applies traction in excess of a predetermined magnitude to the handle ears, the one or more pressure valves move in a proximal direction causing the narrow distal portion of the pressure valves to move so as to become positioned adjacent to the channel thereby opening the channel and the one or more apertures of the stem to the ambient, thereby releasing the suction force on the scalp of the fetus.

In the above embodiment of the second aspect of the invention, the handle member of the vacuum extractor further includes a handle cover spaced apart from the handle ears on the distal side of the handle ears. When traction is applied by the physician the handle cover moves in the proximal direction narrowing the space between the handle cover and the handle ears thereby applying a force to the one or more pressure valves so that they move in the proximal direction. This allows the narrower distal portion of the one or more valves to move adjacent to the channel, opening it and the one or more apertures in the stem to air from the ambient.

In another embodiment of the second aspect of the present invention the traction limiting element of the vacuum extractor includes: a housing and a sealing element in arrangement with the housing. The sealing element is movably fitted on the stem of the extractor and seals off the one or more apertures from the ambient when positioned adjacent to the one or more apertures. When a physician applies traction to the handle member, the sealing element moves in the proximal direction past the one or more apertures and serially opens them to the ambient atmosphere, thereby releasing the vacuum being applied to the scalp of the fetus.

The traction limiting element of the vacuum extractor in this second embodiment of the second aspect of the invention may further include a spring element positioned on a spring base within the housing. The spring element is compressed under a traction force and when the traction force is released the spring element returns to its uncompressed state moving the sealing element in the distal direction to its original position again blocking ambient air from entering the one or more apertures.

The second aspect of the present invention also provides handle members and traction limiters constructed substantially as described above with respect to the traction limiting elements in the vacuum extractors of the second aspect of the invention described above.

BRIEF DESCRIPTION OF THE DRAWINGS

Other objects, advantages and applications of the present invention will be made apparent by the following detailed description of preferred embodiments of the invention. The description makes reference to the accompanying drawings in which:

FIG. 3 is a partial side view of a second embodiment of the invention wherein the digital pressure sensor and a relief valve controlled by the detection of excess pressure by the sensor are located in the vacuum line to the extractor body;

DETAILED DESCRIPTION OF THE PREFERRED EMBODIMENTS

Figure 1:
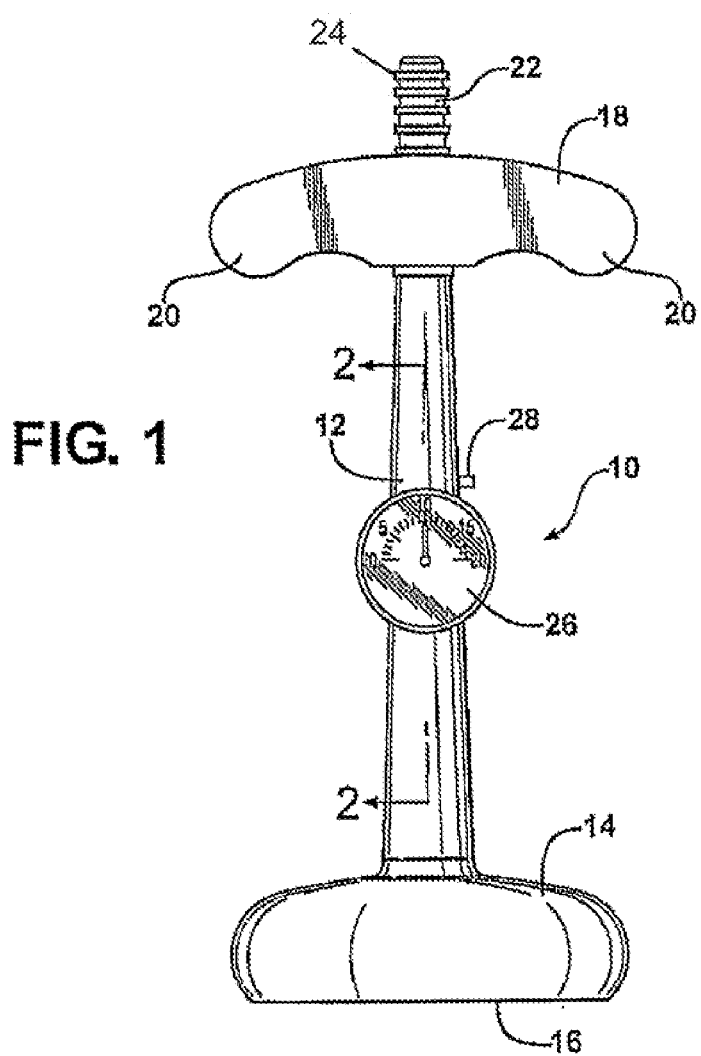
FIG. 1 is a side view of an obstetrical vacuum extractor forming a first embodiment of the invention.

Referring to the drawings, FIG. 1 illustrates a preferred embodiment of my invention constructed on an obstetrical vacuum extractor of the general type illustrated in U.S. Pat. No. 5,019,086. The extractor, generally indicated at 10, has an elongated hollow stem 12, preferably formed of plastic. The lower end of the stem, as illustrated in FIG. 1, is connected to a resilient cup 14 which is open at its lower end 16. The cup is formed as a shell and the interior of the cup 14 communicates with the hollow section of the stem 12.

In alternate embodiments of the invention the cup 14 can be rigid and made of metal, although resilient cups are more popular with obstetricians.

The upper end of the stem 12 is connected to a rigid handle 18 consisting of two ears 20 which project on opposite sides of the connection of the handle to the stem. The upper end of the hollow within the stem is joined to a connector 22 which is adapted to receive a flexible vacuum hose (not shown). A plurality of ribs 24 formed along the length of the connector 22 provides an airtight seal for the connecting air hose.

In use, the open end 16 of the cup 14 is brought into contact with the fetal scalp and a vacuum source is joined to the connector 22. The vacuum source may be mechanically actuated with a pump powered by an assistant, or it may take the form of an electrically powered vacuum device. The suction force from the vacuum device is communicated through the stem 12 to the cup 14 and draws a vacuum which securely retains the open end 16 of the cup in contact with the fetal scalp. The physician then grasps the handle 18 and pulls on the extractor to exert a force on the fetus which assists in the delivery of the fetus through the vagina.

The vacuum extractor 10 differs from conventional vacuum extractors in two respects: First, an analog gauge 26 is positioned on the stem 12 and connected so as to sense the force applied to the fetal scalp by manipulation of the device 10. That value is exhibited on the face of the gauge 26. Secondly, a relief conduit 28 is positioned on the body of the stem so as to connect the interior of the stem, and thus the active area of the cup 16, to atmospheric pressure under certain conditions.

Figure 2:
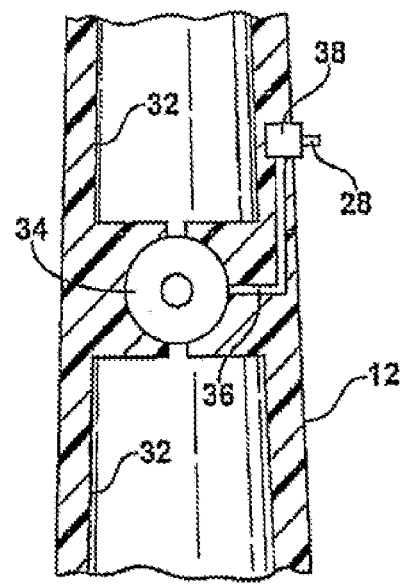
FIG. 2 is a breakaway section through the stem of the extractor of FIG. 1 illustrating the pressure sensor and the relief valve controlled by the pressure sensor.

Referring to FIG. 2, which is a partial cross section through the extractor 10, taken along lines 2-2 of FIG. 1, the stem has an interior hollow 32 which communicates the vacuum from the connector 22 to the fetal scalp through the open end 16 of the cup 14. The vacuum drawn on the scalp passes through the gauge 34, connected to the dial 26. The gauge 34 also generates an electrical signal on output lines 36 when a predetermined value of vacuum, which represents the maximum safe extraction pressure, is exerted. The gauge is preferably battery powered. The lines 36 connect to a valve 38 which connects to the atmosphere through the conduit 28. Thus, when the pressure sensed by the gauge 34 exceeds the predetermined maximum value, the vacuum is connected directly to the atmosphere, relieving the vacuum pressure between the cup 14 and the fetal scalp.

In other embodiments of the invention the gauge 26 could present a digital output and/or the trigger value at which the gauge sends a signal to the valve 38 could be adjusted.

A second embodiment of the invention is illustrated in FIG. 3. The handle end of a vacuum extractor is generally indicated at 40. The vacuum extractor 40 may be identical to the vacuum extractor 10 and to the prior art in that it does not include a gauge 26 or a relief conduit 26; alternatively, in this embodiment of the invention those units are incorporated in the line connecting the vacuum extractor to the vacuum source.

As illustrated in FIG. 3, the handle 18 of the vacuum extractor 40 is equipped with a vacuum inlet port at connector 22 of the same type as illustrated on the extractor 10 of FIGS. 1 and 2. A vacuum source 42, preferably electrically powered, draws a vacuum through a line which is joined to the connector 22 by a female tubular connector 44 which slides over the male connector 22. Also connected in the line 46 is a digital gauge 48, which is preferably adjustable to a predetermined limit decided on by the attending physician, and a relief valve 50 connected to the gauge by line 52. When the limit set on the gauge 48 is reached, a signal is sent to the valve 50 which connects the line 46 to the atmosphere and thus relieves the vacuum on the cup 14 attached to the fetal scalp. The system operates in just the same way as the extractor 10 of FIG. 1, but incorporation of the gauge 48 in the valve 50 and the input line 46 allows the invention to be used with a conventional extractor which does not have its own pressure gauge and relief line.

A vacuum extractor, generally indicated as 100, has an elongated hollow stem 112, preferably formed of plastic. The end of stem 112 closest to the distal end (D) of extractor 100, is connected to a resilient cup 114 which is open at its distal end 116. Cup 114 is formed as a shell and the interior of the cup communicates with the hollow section of stem 112. Alternatively, cup 114 can be rigid and made of metal, although resilient cups are more popular with obstetricians.

A rigid handle 118, comprised of two ears 120, projects from opposite sides of handle housing 158. Housing 158 connects handle 118 to stem 112 at a position distant from cup 114 and in a proximal direction therefrom.

Handle 118, having handle ears 120, is typically integrally formed with handle housing 158 and movably attached to stem 112. Press spring 140 is positioned on spring base 146 within handle housing 158. Spring base 146 is substantially annular-shaped and either may be formed as an integral part of stem 112 or as a separate part fixedly attached to stem 112.

While we have denoted element 140 as a press spring, any other elastic element capable of performing the functions of press spring 140 as described herein may also be used. Typically, but without intending to limit the invention, spring 140 may be formed of metal, but other materials having the required performance characteristics may also be used. Other elastic elements which may be used include elements formed from metals or plastics or other suitable elastomeric materials known to those skilled in the art.

Handle housing 158 is positioned on stem 112 at a position adjacent to apertures 152, 154 and 156, the apertures disposed in stem 112. When vacuum extractor 100, herein also referred to as device or vacuum extractor device or extractor device 100, is not being used, aperture sealing element 159, an integral part of handle housing 158, lies adjacent to apertures 152 and 154 hermetically sealing them and not allowing air from the ambient to enter the hollow 170 of stem 112. When device 100 is not in use, or when the mother is between contractions during the later stages of the birth, aperture 156 is kept open. Aperture sealing element 159 also functions as that portion of housing 158 directly connecting housing 158 to stein 112.

The volume created by handle housing 158 contains press spring 140 and handle housing 158 is open to the ambient at its proximal end near spring base 146.

Flexible tube 122 is force fitted onto proximal end 142 of stem 112. Proximal end 142 of stem 112 may be formed to contain ratchet-like grooves for a better fit with flexible tube 122. Flexible tube 122 is attached to a vacuum suction source (not shown) at its proximal end (also not shown).

It should be evident to persons skilled in the art that other techniques may also be used to connect tube 122 to stem 112. For example, as in the embodiment of the present invention discussed in conjunction with FIGS. 1-3 above, the proximal end of hollow 170 within stem 112 may be joined to a connector (not shown) which is adapted to receive a flexible tube 122. A plurality of ribs (discussed in conjunction with FIGS. 1 and 3) formed along the length of the connector 22 (FIGS. 1 and 3) provides an airtight seal for connecting flexible tube 122 to stem 112.

Vacuum extractor 100 differs from conventional vacuum extractors in several respects. Handle housing 158 rides on press spring 140 and when a user pulls on handle 118, the user exerts a traction force on the fetus in an attempt to accelerate its passage through the birth canal. When traction is exerted, press spring 140 is compressed and handle housing 158 moves in the proximal direction. As housing 158 moves proximally, aperture sealing element 159 first moves proximally covering previously open aperture 156 in addition to covered apertures 152 and 154. When all three apertures are covered, suction provided by a vacuum suction source (not shown) can attain a maximal value. As the traction force exerted by the physician on the handle of device 100 slowly increases and reaches a predetermined value, sealing element 159 sequentially passes apertures 152 and 154 in tube 112 allowing them to open and the suction being applied to the fetus via cup 114 to be progressively released. Opening aperture 152 partially releases the suction on the scalp of the fetus; when sealing element 159 moves further in the proximal direction aperture 154 opens and the suction is entirely released. As noted above, movement of aperture sealing element 159 is a function of the traction exerted by the physician. Therefore, handle housing 158 and aperture sealing element 159 function as a traction limiter in the fetal extraction process.

Optionally, an indicator strip 148 is positioned on stem 112 at least partially underneath handle housing 158. Strip 148 appears and becomes progressively larger as handle housing 158 moves progressively along stem 112 in the proximal direction. As traction increases, indicator strip 148 provides the user with a qualitative indication of how much traction force is being applied. It should readily be understood by persons skilled in the art that the indicator can be calibrated against specific predetermined traction forces so that a more quantitative value for the traction force actually being applied may be obtained.

When in use, the open distal end 116 of cup 114 is brought into contact with the fetal scalp and a vacuum source (not shown) is joined to flexible tube 122 which in turn is in suction communication with stem 112 and cup 114. The vacuum source may be mechanically actuated with a pump powered by an assistant, or it may take the form of an electrically powered vacuum device. Other types of vacuum sources may also be used.

The suction force from the vacuum source is communicated through flexible tube 122 to hollow 170 of stem 112 and from there to cup 114. The vacuum securely retains the open end 116 of cup 114 in contact with the fetal scalp. The physician then grasps and pulls on the two ears 120 of handle 118 in the proximal direction (P) to exert a force on the fetus which assists in the delivery of the fetus through the vagina.

Reference is now made to FIGS. 5A-5D, where several different views of a second embodiment of the second aspect of the invention are presented.

Figures 5A, 5B, 5C, 5D:
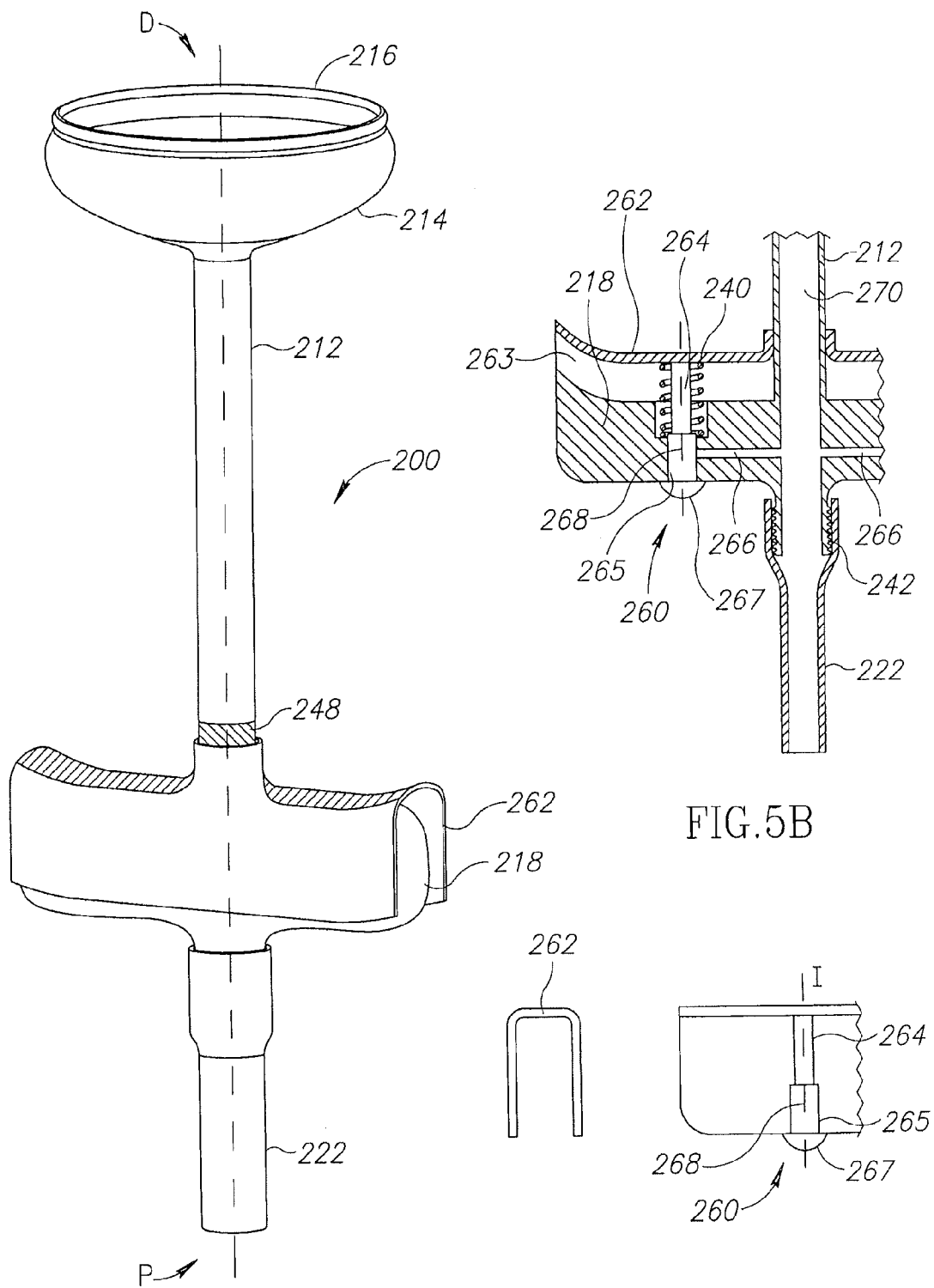
FIG. 5A is a side view of a second embodiment of the second aspect of the present invention.
FIG. 5B is a partial cutaway side view of the handle region of the extractor shown in FIG. 5A.
FIG. 5C is another less detailed cutaway side view of the handle and pressure valve of the embodiment shown in FIG. 5A.
FIG. 5D is a cross section of the handle cover in the embodiment of FIGS. 5A-5C.

In FIG. 5A a slightly off-angle side view of a vacuum extractor device, generally referred to as 200, is shown. Extractor 200 has an elongated hollow stem 212, preferably, but not necessarily, formed of plastic. The end of stem 212 closest to the distal end (D) of extractor 200 is connected to a resilient cup 214 which is open at its distal end 216. Cup 214 is formed as a shell and the interior of the cup communicates with the hollow 270 (FIG. 5B) of stem 212. An optional indicator strip 248 is shown as is handle 218. A flexible tube 222 force fitted over the proximal end 242 (FIG. 5B) of stein 212 also appears in the Figure. This proximal end 242 of stem 212, best seen in FIG. 5B, may have ratchet-like grooves for a better fit with the distal end of flexible tube 222. Handle 218 has a handle cover 262 which is spaced apart from handle 218 by space 263 (FIG. 5B). FIG. 5D is a transverse cross-section of handle cover 262.

Referring now to FIGS. 5B and 5C, suction from a vacuum source (not shown) is brought to cup 214 via flexible tube 222 and stem 212 and is applied to the scalp of a fetus. When a user applies traction to device 200, the hand of the user presses on handle cover 262. This traction causes cover 262 to move in the proximal direction (P) so that it compresses press spring 240. Press valve 260 is fixedly connected with handle cover 262, the connection being effected by any of many different methods known in the art. Press valve 260 may be made of plastics or metal, for example, but without attempting to limit the invention, acrylonitrile/butadiene/styrene (ABS) or stainless steel. Methods for fixedly connecting handle cover 262 to press valve 260 may be gluing, ultrasonic welding, injection or insertion molding or any other suitable method. As handle cover 262 is pressed moving in the proximal direction, it compresses press spring 240 and presses on press valve 260 causing it to move in the proximal direction.

Press valve 260 is comprised of a smaller diameter part 264, a larger diameter part 268, and a lock portion 267. The larger diameter part 268 is substantially equal to the diameter of an air passage 265 in which press valve 260 is positioned. Large diameter part 268 is sized to substantially close the entrance of an air channel 266 at its juncture with air passage 265. As handle cover 262 presses press spring 240 and concomitantly as press valve 260 moves in the proximal direction, the large diameter part 268 of valve 260 moves past air channel 266 and is replaced by Smaller diameter part 264 at the entrance of air channel 266. This allows air from the ambient entering via handle space 263 and air passage 265 to enter air channel 266. The opening of channel 266 occurs at a predetermined traction force value. As air from channel 266 enters hollow 270 of stem 212, suction is immediately released and cup 214 detaches from the head of the fetus.

When the traction force is released, handle 218 moves in the distal direction returning to its original position. Press valve 260 and press spring 240 will also return to their original positions by moving in the distal direction. Handle cover 262 also moves in the distal direction returning to its original position and lock part 267 of press valve 260 helps keep handle cover 262 from separating from press valve 260.

Press valve 260 and press spring 240 as described above function as a traction limiter in the fetal extraction process.

Typically, but without intending to limit the invention, press spring 240 may be formed of metal but other materials having similar performance characteristics may also be used. Elastic elements capable of performing the functions of press spring 240 as described herein may also be used. Such elements may be formed from metals, plastics or elastomers having performance characteristics similar to those of press spring 240.

Optionally, as in the previous embodiment, an indicator strip 248 (FIG. 5A) is positioned on stem 212, at least partially underneath handle cover 262. Strip 248 becomes progressively larger as handle cover 262 moves progressively along stein 212 in the proximal direction when cover 262 is pressed. As traction increases, indicator strip 248 provides the user with a qualitative indication of how much traction force is being applied. It should readily be understood by persons skilled in the art that the indicator can be calibrated against specific predetermined traction forces so that a more quantitative value for the traction force actually being applied may be obtained.

FIGS. 5B and 5C show two different partial side views of handle 218 and/or handle cover 262. Both sides of handle 218 are not shown. However, it should be readily understood that handle 218 may be symmetrical on both sides of stem 212 with a press valve 260, an air passage 265 and an air channel 266 present on both sides of stem 212. Alternatively, the valve on the second side (not shown) of handle 218 may be a dummy valve with no air channel 266 connection to hollow 270 of stem 212. Alternatively, there may be no valve, real or dummy, on the second side (not shown) of handle 218.

Most of the elements in the embodiments discussed in conjunction with FIGS. 4A-5B are made of plastic. For example, but without limiting the types of plastic which may be used, stem 112, 212 and cup 114, 214 may be made from high density polyethylene (HDPE), handles 118, 218, press valve 260 and handle cover 262 may be made from acrylonitrile/butadiene/styrene (ABS), and flexible tube 122, 222 may be made from silicone, polyvinyl chloride (PVC) or polyurethane (PU). Springs 140 and 240 may be made of stainless steel.

Figure 4A:
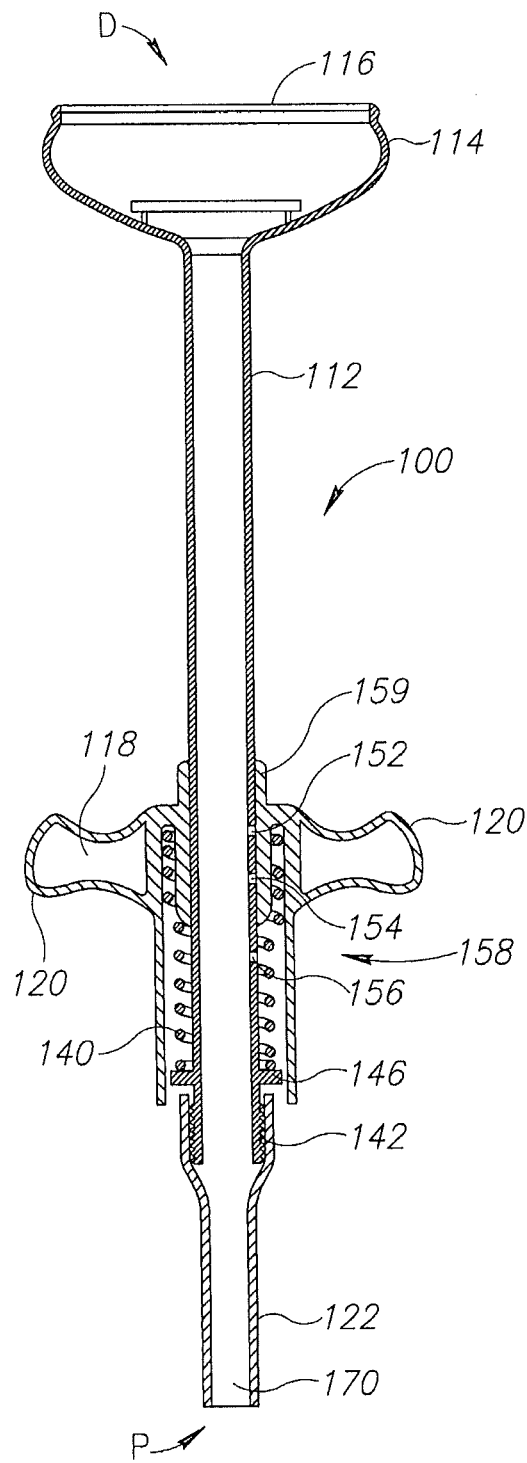
FIGS. 4A and 4B are a cut away side view and a regular side view of a first embodiment of a second aspect of the present invention.
Figure 4B:
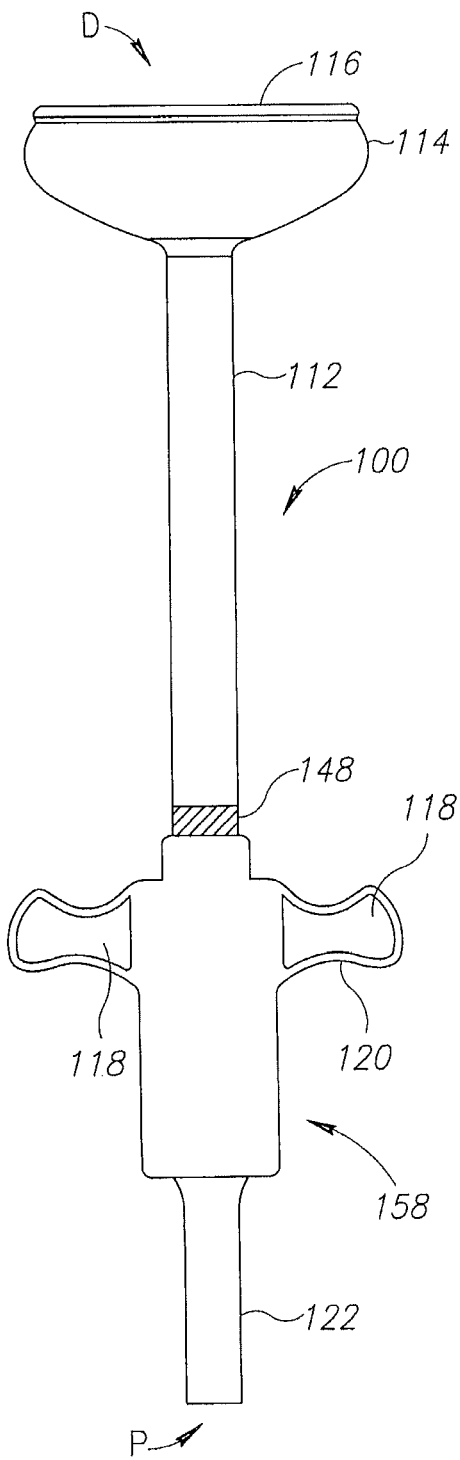
Figure 6A:
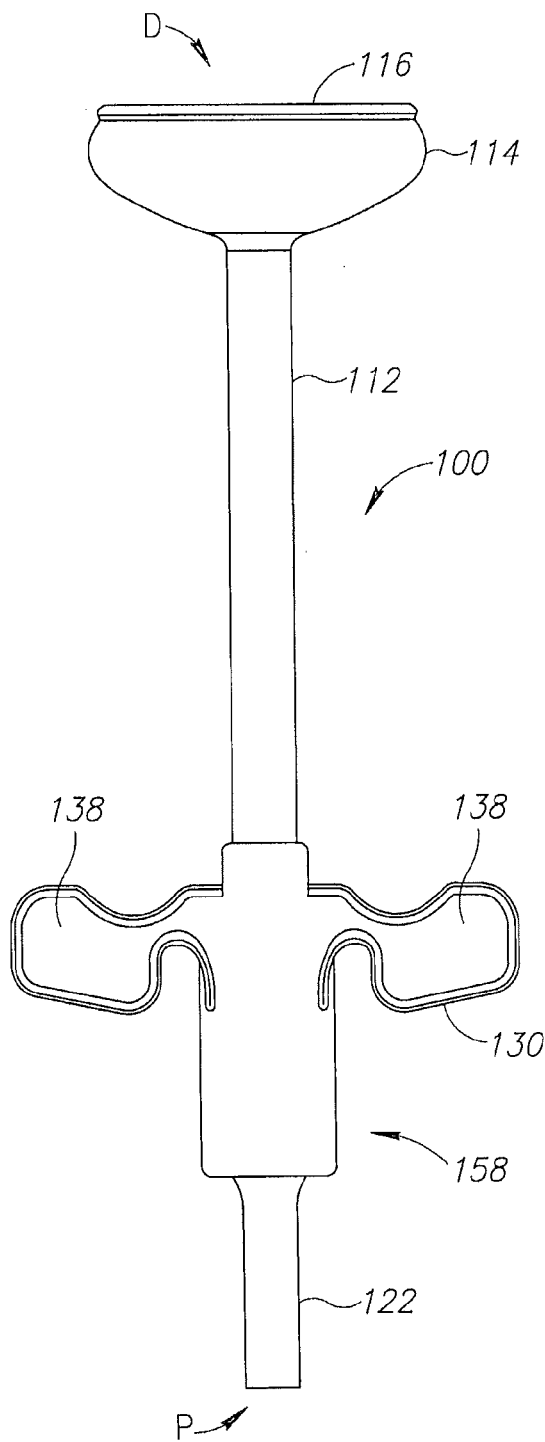
FIGS. 6A-6B illustrate a third embodiment of the second aspect of the present invention, the embodiment having collapsible or bendable handles.
Figure 6B:
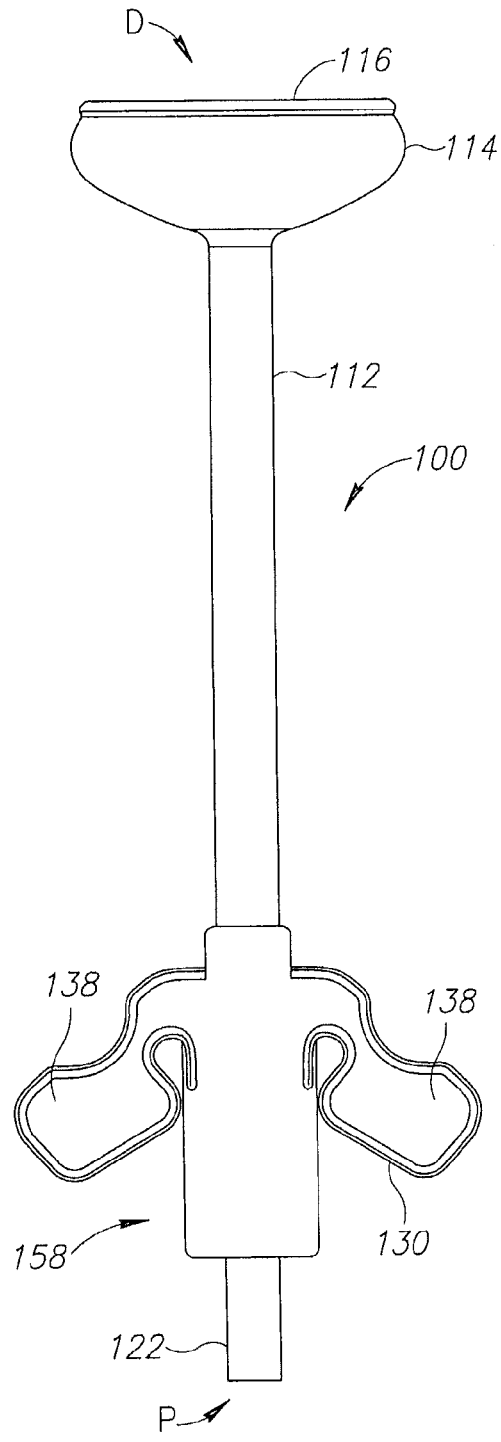

In a third embodiment of the second aspect of the invention, shown in FIGS. 6A and 6B, a vacuum extractor similar to the one shown in FIG. 4B and discussed above is presented. With the exception of handle 130 and handle ears 138, all parts in FIGS. 6A and 6B are the same as those in FIG. 4B. Accordingly, the construction and operation of those parts will not be discussed again. Handle 130 and handle ears 138 may be formed from a suitable plastic of the required mechanical strength and configured so that ears 138 collapse or severely bend when a predetermined traction force is reached. This would indicate that the vacuum source (not shown) must be immediately disconnected. A typical but none limiting configuration for the handle is presented in FIG. 6A. Here, handle ears 138 of handle 130 are configured to bend or collapse as a result of the narrow constrictions in the region where handle ears 138 join handle housing 158. It should be readily evident to persons skilled in the art that the use of collapsibly configured handle ears 138, similar to those shown in FIGS. 6A and 6B, may be used with many other types of vacuum extractors as a means for indicating that excess traction force is being applied and should be limited. These collapsible configurations need not be used solely with the embodiments shown in FIGS. 4A-5B.

Figures 7A, 7B:
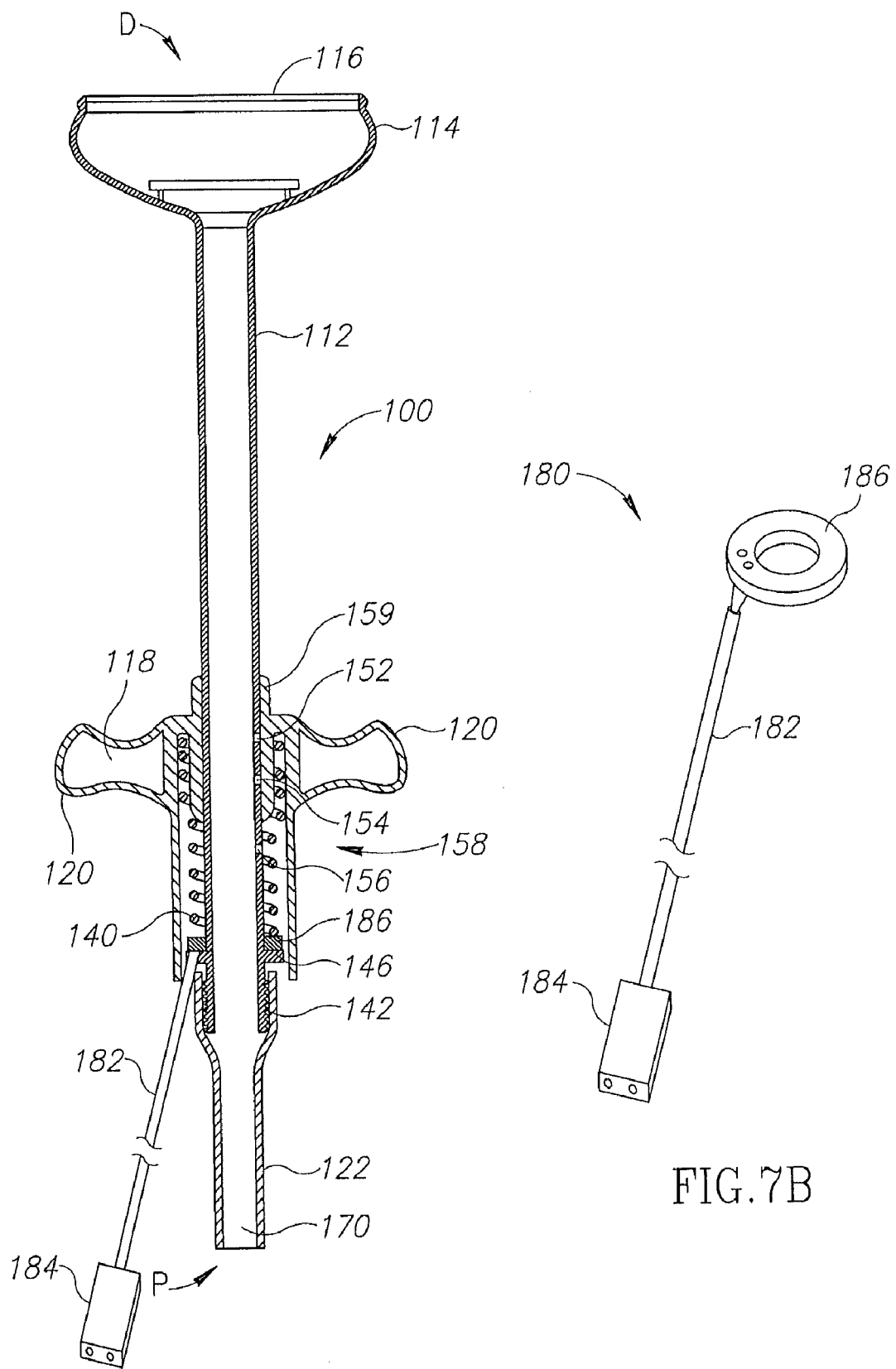
FIG. 7A is a cutaway side view of a fourth embodiment of the second aspect of the present invention.
FIG. 7B is a perspective view of a force load sensing element used in the embodiment shown in FIG. 7A.

In a fourth embodiment of the second aspect of the invention, shown in FIGS. 7A and 7B, a vacuum extractor 100 similar to the one shown in FIG. 4A, and discussed above is presented. With the exception of a load sensing element 180, shown in FIG. 7B separately and in FIG. 7A as part of vacuum extractor 100, all parts in FIG. 7A are the same as those in FIG. 4A. Accordingly, the construction and operation of those parts will not be discussed again.

As seen in FIG. 7B, electrical force load sensing element 180 comprises an annular ring member 186 and electrical wires 182, the latter connected to an electrical connector 184. Electrical connector 184 may be connected to an alarm element (not shown), such as a buzzer, or the vacuum source (also not shown) or both. The electronic signal of load sensing element 180 or the circuit to which it is connected, may be activated, at a predetermined over-traction force, to buzz noisily, or to release the vacuum in the vacuum source, or to do both.

FIG. 7A shows the integration of force load sensing element 180 into vacuum extractor 100. Force load sensing element 180 is positioned on spring base 146. As press spring 140 becomes more and more compressed under traction, the load in load sensing element 180 increases. At a predetermined value of traction force, that is reflected in the degree of press spring 140 compression, an alarm system, such as a buzzer, is activated alerting the physician to deactivate the vacuum source or the vacuum source itself is automatically electronically deactivated using suitable electronics. The required electronic circuitry may readily be constructed and configured by persons skilled in the art.

Typically, the over-traction forces which cause the exposure of aperture 152 and then aperture 154 of FIGS. 4A-4B may be 17 and 18 kgs respectively and the over-traction force that causes air to flow through the air channel(s) 266 of FIG. 5B is 18-20 kgs with a 6 cm cup diameter and 14 kgs with a 5 cup diameter. These are over-traction forces that can be used with embodiments employing the bendible/collapsible handle ears of FIGS. 6A-6B. Open aperture 156 of FIGS. 4A-4B is, as noted above, the default position before full suction is applied to the fetal scalp and before the physician applies traction to handle 118. Aperture 156 is also kept open between contractions during the birthing process when it lowers the suction on the fetal scalp from about 600 mm Hg to about 500 mm Hg. However, it should be readily evident to persons skilled in the art that these over traction values and cup sizes can be modified as desired subject to the physiological and anatomical constraints of the fetus and mother.

Where the terms "physician" and "user" are used herein it should readily be understood that these terms may include any birthing attendant that would have occasion to use a vacuum extractor during a birth.

It is to be understood that the invention is not limited to the exact details of construction, operation, exact materials, or embodiments shown and described, as modifications and equivalents will be apparent to one skilled in the art. Accordingly, the invention is therefore to be limited only by the scope of the appended claims.

Having thus described my invention, we claim:

1. A vacuum extractor for use by a physician in an obstetrical delivery, the vacuum extractor in suction communication with a vacuum source and comprising:
    an elongated hollow stem having a plurality of apertures serially positioned along its length;
    a cup supported on one end of the stem, an open end of the cup directed away from the stem, the vacuum source connected to an interior of the cup so that when the plurality of apertures is closed and the open end of the cup is brought into contact with a scalp of a fetus a vacuum secures the cup to the scalp of the fetus; and
    a handle member disposed on the stem, the handle member including:
    handle ears; and
    a traction-limiting element in arrangement with the handle ears and operative to open and close the plurality of apertures serially positioned along the length of the stem,
    wherein when no traction is applied by the physician to the handle ears the traction-limiting element blocks air flow from an ambient atmosphere through the plurality of apertures to the stem and when the physician applies traction to the handle ears, when a magnitude of the traction exceeds a predetermined value, the traction-limiting element is operative to sequentially open the plurality of apertures allowing an increasing flow of air from the ambient atmosphere to reduce the vacuum on the scalp of the fetus between contractions of a birthing process.

2. The vacuum extractor of claim 1, wherein the fraction-limiting element comprises:
    a housing; and
    a sealing element in arrangement with the housing and movably fitted on the stem of the extractor, the sealing element sealing off the plurality of apertures from the ambient atmosphere when positioned adjacent to the plurality of apertures,
    wherein when the physician applies traction to the handle member, the sealing element moves in a proximal direction past the plurality of apertures opening them to the ambient atmosphere, thereby reducing the vacuum applied to the scalp of the fetus between contractions of the birthing process.

3. The vacuum extractor of claim 2, wherein the traction-limiting element further includes a spring element positioned on a spring base within the housing, the spring element compressed under a traction force and when the traction force is released the spring element returns to an uncompressed state moving the sealing element in a distal direction to an original position again blocking the plurality of apertures from air entering from the ambient atmosphere.

4. The vacuum extractor of claim 3, further comprising a load-sensing element positioned in mechanical communication with the spring element and operable to sense traction force applied by a physician to the handle ears, the load-sensing element in electrical communication with the vacuum source or an alarm element and operable to deactivate the vacuum source or to activate the alarm element when a predetermined traction force has been attained.

5. The vacuum extractor of claim 2, wherein the handle ears are constructed of material and configured to bend or collapse under a predetermined traction value, thereby alerting the physician to deactivate the vacuum source.

6. The vacuum extractor of claim 1, wherein the cup has a resilient edge.

7. The vacuum extractor of claim 1, wherein the cup has a rigid edge.

8. The vacuum extractor of claim 1, further comprising a visual indicator which provides information to the physician as to suction force applied to the scalp of the fetus by the vacuum source.

9. The vacuum extractor of claim 1, wherein the stem includes a male connector and the extractor is adapted to receive one end of a vacuum line connected to the vacuum source and slipped over the male connector.

10. A handle member for controlling an obstetrical vacuum extractor, the extractor including an elongated hollow stem having a plurality of apertures serially positioned along its length, a cup at a first end of the stem and a vacuum source for applying a vacuum to an interior of the cup while it is pressed against a scalp of a fetus so as to secure the cup and the extractor to the scalp of the fetus, the handle member comprising:
    handle ears; and
    a traction-limiting element in arrangement with the handle ears and operative to open and close the plurality of apertures serially positioned along the length of the elongated hollow stem,
    wherein when no traction is applied by a user to the handle ears the traction-limiting element blocks air flow from an ambient atmosphere through the plurality of apertures to the stem and when the user applies traction to the handle ears, when a magnitude of the traction exceeds a predetermined value, the traction-limiting element is operative to sequentially open the plurality of apertures allowing flow of air from the ambient atmosphere to reduce the vacuum on the scalp of the fetus between contractions of the birthing process.

11. The handle member of claim 10, wherein the predetermined magnitude of traction may be adjusted.

12. The handle member of claim 10, wherein the traction-limiting element comprises:
 a housing; and
 a sealing element in arrangement with the housing and movably fitted on the stem of the extractor, the sealing element sequentially sealing off the plurality of apertures serially positioned along a length of the stem from the ambient atmosphere when positioned adjacent to the plurality of apertures;
 wherein when the user applies traction to the handle member, the sealing element moves in a proximal direction past the plurality of apertures opening them to the ambient atmosphere, thereby reducing the vacuum applied to the scalp of the fetus between contractions of the birthing process.

13. The handle member of claim 12, wherein the traction-limiting element further includes a spring element positioned on a spring base within the housing, the spring element compressed under a traction force and when the traction force is released the spring element returns to an uncompressed state moving the sealing element in a distal direction to an original position again blocking the plurality of apertures from the ambient atmosphere.

14. The handle member of claim 13, further comprising a load-sensing element positioned in mechanical communication with the spring element and operable to sense traction force applied by a user to the handle ears, the load-sensing element in electrical communication with the vacuum source or an alarm element and operable to deactivate the vacuum source or to activate the alarm element when a predetermined traction force has been attained.

15. The handle member of claim 13, wherein the handle ears are constructed of material and configured to bend or collapse under a predetermined traction value, thereby alerting the user to deactivate the vacuum source.

* * * * *